United States Patent
Cheiky-Zelina et al.

(10) Patent No.: US 6,204,656 B1
(45) Date of Patent: Mar. 20, 2001

(54) MINIATURE SENSOR FOR LUBRICANT ANALYSIS

(75) Inventors: Margaret A. Cheiky-Zelina, Cleveland; Wayne A. Bush, Wooster, both of OH (US)

(73) Assignee: Reid Asset Management Company, Willoughby Hills, OH (US)

(*) Notice: Subject to any disclaimer, the term of this patent is extended or adjusted under 35 U.S.C. 154(b) by 0 days.

(21) Appl. No.: 08/865,503

(22) Filed: May 29, 1997

(51) Int. Cl.$^7$ .................................................. G01R 27/26

(52) U.S. Cl. ..................... 324/71.4; 324/204; 324/687; 340/631

(58) Field of Search ........................... 340/631; 324/71.4, 324/204, 687, 690

(56) References Cited

U.S. PATENT DOCUMENTS

| | | |
|---|---|---|
| 3,233,173 | 2/1966 | Lees et al. . |
| 4,047,814 | 9/1977 | Westcott . |
| 4,423,371 | 12/1983 | Senturia et al. . |
| 4,503,383 * | 3/1985 | Agar ..................................... 324/663 |
| 4,689,553 | 8/1987 | Haddox . |
| 5,025,222 | 6/1991 | Scott et al. . |
| 5,045,798 | 9/1991 | Hendrick . |
| 5,072,190 | 12/1991 | Martin . |
| 5,260,665 | 11/1993 | Goldberg et al. . |
| 5,262,732 | 11/1993 | Dickert et al. . |
| 5,317,252 | 5/1994 | Kranbuehl . |
| 5,334,941 | 8/1994 | King . |
| 5,457,396 | 10/1995 | Mori et al. . |
| 5,504,573 | 4/1996 | Cheiky-Zelina . |
| 5,540,086 | 7/1996 | Park et al. . |
| 5,548,217 | 8/1996 | Gibson et al. . |
| 5,596,266 | 1/1997 | Mori et al. . |
| 5,604,441 * | 2/1997 | Freese ................................. 324/663 |

OTHER PUBLICATIONS

Iotech Catalog, p. 65, Jan. 1995.*
"Model 958PF On–Line Ferrograph", *Foxboro Analytical*, 1980, 4 pgs.*
"958PF Series On–Line Ferrograph Installation and Operation", The Foxboro Company, 1980, 6 pgs.*
"Journal Reprints", The British Institute of Non–Destructive Testing, M. H. Jones and A. R. Massoudi, Insight, vol. 37, No. 8, Aug., 1995, pp. 606–610.*
"Basics of Measuring the Dielectric Properties of Materials", Hewlett Packard, 1992.*
"The NIST 60–Millimeter Diameter cylindrical Cavity Resonator: Performance Evaluation for Permittifity Measurements", Eric J. Vanzura, Richard G. Geyer and Michael D. Janezic, Aug. 1993, National Institute of Standards and Technology Technical Note.*

* cited by examiner

Primary Examiner—Josie Ballato
Assistant Examiner—Jose M. Solis
(74) Attorney, Agent, or Firm—Renner, Otto, Boisselle & Sklar

(57) ABSTRACT

A fluid contamination analyzer employs one or more micro-miniature sensors which provide for a substantial reduction in sensor dimensions form prior art dimensions of approximately 2 in.×2 in. to approximately 1 mm×1 mm. The sensors are incorporated into probes for easy lubricant fluid accessibility or alternatively may be employed in an on-line analyzer residing in the fluid flow path. The sensors sense an impedance of the fluid which is a function of its contamination and communicates the impedance to analysis circuitry via either a hard-wired or RF data link. An array of sensors may also be utilized in conjunction with a magnetic field intensity gradient to obtain a particulate distribution across the array. Impedance information, which is indicative of the particulate distribution, is communicated to analysis circuitry individually or in a multiplexed format for fluid contamination analysis. The use of micro-miniature sensors allows for substantial improvements in fluid contamination analysis by making fluid analysis procurement easy while increasing the number of applications in which such analysis may be employed.

21 Claims, 4 Drawing Sheets

MINIATURE SENSOR FOR LUBRICANT ANALYSIS

FIELD OF THE INVENTION

The present invention relates generally to an apparatus and method for analyzing fluids such as lubricants. More particularly, the invention relates to a miniature sensor for detecting and monitoring conditions of a fluid such as water content, oxidation and metallic or conductive particle contamination.

BACKGROUND OF THE INVENTION

The presence of corrosive products, contaminants, metallic particles, oxidation, etc., in fluids such as lubricants can cause problems. For example, contaminants in lubricants can lead to damage of machinery in which the lubricant is utilized, causing unnecessary or accelerated wear on the lubricated members.

Various approaches have been developed to detect conditions such as deterioration or contaminants in fluids. One conventional system described in U.S. Pat. No. 4,646,070 utilizes a pair of capacitor electrodes positioned in a fluid. The fluid serves as a dielectric between the electrodes to develop a frequency voltage signal across the capacitor electrodes. Based on such signal, the dielectric and deterioration of the fluid is determined. This solution suffers from a drawback because the sensor is large and bulky and is difficult to move from machine to machine to make fluid contamination measurements.

U.S. Pat. No. 5,262,732 describes a system which utilizes an oscillator circuit coupled to a capacitive sensor. The fluid under test is placed in a reservoir containing the capacitive sensor and the oscillator circuit generates a signal having a frequency that increases or decreases depending on the capacitance of the sensor. The system of U.S. Pat. No. 5,262,732 is also rather large and cumbersome and does not lend itself to portability. In the field, it would be difficult to transport the device from machine to machine to analyze the lubricant at the location of the machinery, for example.

In addition, prior art sensors have been rather large so that a user could insert the sensor into the fluid and thereby remove a fluid sample from a machine for analysis. This large, sturdy construction also allowed the sensor to be subsequently cleaned for use at another machine without causing damage to the sensor. Unfortunately in some machines, obtaining a manual fluid sample with a large, unwieldy sensor is inconvenient due to machine construction. Also, in some applications one wishes to affix a lubricant analysis sensor to the machine in the lubricant fluid flow path (called an on-line configuration) in order that a user may merely attend the machine and obtain a lubricant contamination reading without having to insert an analyzer apparatus into the fluid flow path. In some cases, prior art sensors are too large and unwieldy and do not conveniently affix to the machine without interfering with proper machine operation.

Figure 5:
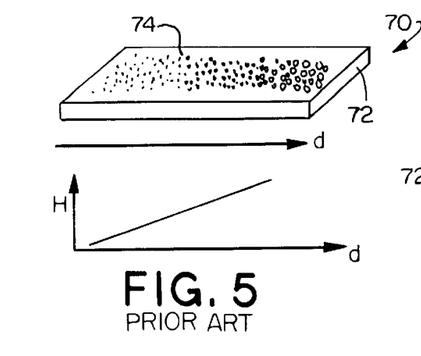
FIG. 5 is a perspective view illustrating a prior art fluid particulate distribution due to a magnetic field intensity gradient.

As disclosed in U.S. Pat. Nos. 4,047,814 and 5,504,573 magnetic field gradients have been utilized to precipitate conductive or ferromagnetic particulates out of a sample fluid (e.g., a lubricant) such that particulates of varying sizes are withdrawn along a horizontal strip for subsequent analysis as illustrated in prior art FIG. 5 of this application. Knowledge of the particulate size distribution is then utilized to determine the status of machinery wear and the potential for failures from wearing parts, etc. Prior to U.S. Pat. Nos. 4,047,814 and 5,504,573 this method relied upon a visual analysis of particulate distribution which was a strong function of the technician's experience performing the analysis, thereby leading to inconsistent conclusions. In addition, since the horizontal strip was removed for analysis, evaluation of the fluid at the machine site was difficult and, in many cases, impossible.

Figure 6:
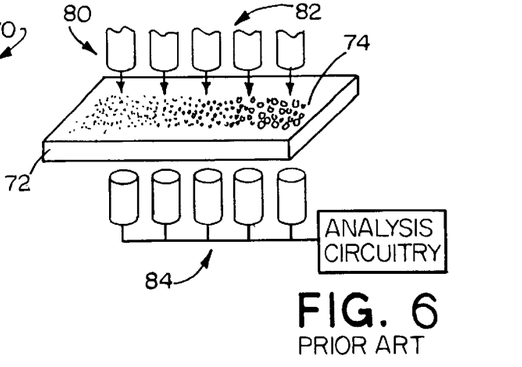
FIG. 6 is a perspective view illustrating a prior art fluid particulate distribution analyzed by a plurality of radiation sources and photodetectors electrically coupled to analysis circuitry.

U.S. Pat. Nos. 4,047,814 and 5,504,573 provided analysis improvement over the manual analysis by illuminating the particulate distribution with radiation and detecting the radiation via a plurality of photodetectors that traverse the particulate sample. Subsequently, the particulate distribution data was obtained via data processing techniques as illustrated in prior art FIG. 6 of this application. Although such a technique provides for an improvement in subsequent analysis conclusions, this technique does not overcome the requirement that an operator initially procure the particulate distribution and send it off-site for analysis. The particulate distribution must still be removed for analysis which limits the locations in which such analysis materials may be located and, in some cases, prohibits their use altogether. Further, if one wishes to affix the particulate distribution collection apparatus with its analysis equipment so that the horizontal strip need not be removed from the machine, the radiation source and photodetectors are undersireably large and thereby further limit the scope of their application.

In view of the aforementioned shortcomings associated with existing systems for analyzing conditions of a fluid such as a lubricant, there is a strong need in the art for a fluid screening device which provides detailed information regarding the particular types of contamination, degree of oxidation or other deterioration, etc. Moreover, there is a strong need in the art for such a screening device which is miniature and thereby provides for ease of lubricant contamination status procurement for machine predictive maintenance programs.

SUMMARY OF THE INVENTION

A fluid contamination analyzer employs one or more micro-miniature oil sensors (MOS) which provide a substantial reduction in sensor dimensions from prior art dimensions of approximately 2 in.×2 in. to approximately 1 mm×1 mm. The sensors are incorporated into probes for easy lubricant fluid accessibility or alternatively may be employed in an on-line analyzer residing in the fluid flow path. The sensors sense an impedance of the fluid which is a function of its particulate contamination and communicates the impedance to analysis circuitry via either a hard-wired or RF data link. An array of micro-miniature sensors may also be utilized in conjunction with a magnetic field intensity gradient to obtain a particulate distribution across the array. Impedance information, which is indicative of the particulate distribution, is communicated to analysis circuitry individually or in a multiplexed format for fluid contamination analysis. The use of micro-miniature sensors allows for substantial improvements in fluid contamination analysis by making fluid analysis procurement easy while increasing the number of applications in which such analysis may be employed.

According to one aspect of the invention, a fluid contamination analyzer includes a probe and at least one micro-miniature sensor at one end of the probe. The sensor includes a substrate and a plurality of conductors above the substrate, wherein each of the conductors is coupled to one of two leads. The conductors form electrodes of the sensor such that when a fluid contacts the sensor an impedance of the fluid may be determined across the sensor leads. In this manner, the fluid contamination analyzer provides an indication of fluid contamination.

According to another aspect of the invention, an on-line fluid contamination analyzer includes an array of micro-miniature sensors located within a path of fluid flow and a selectively activatable magnetic field source (such as a coil) in proximity to the array of micro-miniature sensors. The magnetic field source may be activated and deactivated in response to control signals and provides a magnetic gradient across the sensor array, and the magnetic gradient results in a particulate contaminant size distribution across the sensor array. The particulate size distribution is then sensed electrically via the sensors via the impedance sensed across their leads, thereby providing particulate size distribution data.

In yet another aspect of the invention, a fluid contamination analyzer includes an array of micro-miniature sensors at one end of a probe. At least one sensor includes a substrate and a plurality of conductors formed above the substrate, wherein each conductor is coupled to one of two leads. Another sensor in the array includes a substrate and a plurality of conductors formed above the substrate. Each of the conductors is coupled to one of two leads and is covered with an insulating film. The conductors form electrodes of the sensors and when a fluid contacts the sensors an impedance of the fluid may be determined using the leads of the sensors, thereby providing an indication of fluid contamination. The insulating film prevents the shorting out of electrodes due to the presence of conductive particulates therebetween and provides an indication of non-particulate fluid contamination such as water content and fluid oxidation.

In another aspect of the invention, a fluid contamination analyzer having a micro-miniature sensor includes a substrate and a plurality of conductors above the substrate. Each conductor is coupled to one of two leads and forms electrodes of the sensor such that when a fluid contacts the sensor an impedance of the fluid may be determined using the leads of the sensor. In this manner, an indication of fluid contamination is provided. In addition, a conductive layer overlies the conductors without contacting them such that a cavity for fluid flow analysis is created therebetween. When a voltage is applied to the conductive layer, an electrostatic field is created within the cavity which dislodges conductive particulates that may have become stuck within the sensor due to residual static charge residing on the particulates. The fluid flow through the cavity then carries the dislodged particulates away and thereby improves fluid contamination analysis accuracy by eliminating measurement errors induced by particulates containing static charge.

In yet another aspect of the invention, an on-line fluid contamination analyzer includes an array of micro-miniature sensors located within a path of fluid flow. Each sensor includes a plurality of conductors having a conductor spacing. At least one of the sensors within the array varies in its conductor spacing from the others. A selectively activatable magnetic field source (such as a coil) is placed in proximity to the array of micro-miniature sensors such that upon its activation in response to control signals, a magnetic field intensity gradient is generated across the sensor array, thereby resulting in a contaminant size distribution across the sensor array.

In another aspect of the invention, a fluid contamination system includes one or more machines that employ a lubricant or cooling fluid, having an associated on-line fluid analyzer. The one or more on-line fluid analyzers have at least one micro-miniature sensor having a substrate and a plurality of conductors above the substrate and each conductor is coupled to one of two leads. The conductors form electrodes of the sensor and when the lubricant or cooling fluid contacts the sensor an impedance of the fluid is determined using the leads of the sensor, thereby providing an indication of fluid contamination. The fluid contamination system further includes a communications circuit coupled to the sensor for receiving the impedance of the fluid. The communications circuit is operable to transmit the impedance to another communications circuit in a data analysis circuit which includes a communications circuit and a processor. The communications circuit is operable to electrically communicate (via RF signals and communication protocols, for example) with the fluid analyzer communications circuit and thereby ascertain the impedance of the fluid and determine the level of fluid contamination via the processor without a user manually procuring the fluid sample.

To the accomplishment of the foregoing and related ends, the invention comprises the features hereinafter fully described and particularly pointed out in the claims. The following description and drawings set forth in detail certain illustrative embodiments of the invention. These embodiments are indicative, however, of merely a few of the various ways in which the principles of the invention may be employed. Other objects and advantages of the invention will become apparent from the following detailed description of the invention when considered in conjunction with the drawings.

DETAILED DESCRIPTION OF THE INVENTION

The present invention will now be described with reference to the drawings wherein like reference numerals are used to refer to like elements throughout. As will become more apparent based on the following description, a fluid contamination analyzer for monitoring contaminants in lubricating fluids utilizes micro-miniature sensors, thereby substantially reducing the sensor dimensions and resulting in a greater variety of machine fluid analysis applications. The micro-miniature sensor fabrication techniques also allow for a substantial reduction in sensor costs and provides high sensor manufacturability. Such fabrication techniques also allow for a substantial number of sensor variations with a sensor array for collecting a variety of types of data relating to fluid contamination.

Figure 1:
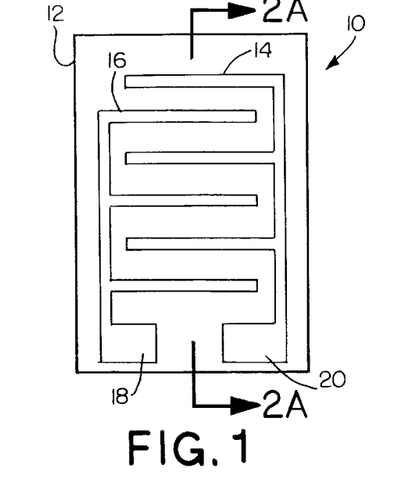
FIG. 1 is a top view of a micro-miniature sensor according to the invention.

FIG. 1 is a top view of a micro-miniature sensor 10 formed using semiconductor fabrication techniques. The sensor 10 includes a substrate 12, preferably made of silicon, upon which a conductive layer, preferably aluminum, is formed and etched to create a pair of interdigitated conductors 14 and 16, respectively. The line widths of the conductors 14 and 16 are preferably 1 micron wide and equally spaced but may be larger or smaller as desired. The first conductor 14 forms a first electrode 14 while the second conductor 16 forms a second electrode 16. Each electrode 14 and 16 are electrically isolated from one another and may be coupled to either discrete instrumentation or circuits integrated with the substrate 12 or other integrated circuits via bond pads 18 and 20, respectively. Since the sensor 10 is fabricated using conventional semiconductor processing techniques, fine line width geometries may be constructed thereby allowing the sensor 10 dimensions to be 1 mm×1 mm or smaller.

The sensor 10 operates in the following manner. When the sensor 10 comes into contact with a fluid sample, the fluid acts as a dielectric between the electrodes 14 and 16 thereby impacting the capacitance (or impedance) of the sensor. Since the capacitance of the sensor 10 can be characterized by $C=\epsilon A/d$, wherein A is the electrode surface area (which is known) and d represents the electrode spacing (which is also known), the measured capacitance provides an indication of the properties of the dielectric (the fluid). Therefore the sensor 10 senses the capacitance (and therefore the impedance) of the fluid at its leads (bond pads 18 and 20) and provides this value at the bond pads 18 and 20 for analysis by analysis circuitry (not shown). The analysis circuitry takes the impedance value and determines the level of fluid contamination based upon either a comparison with a known clean fluid sample or with an expected value. Various methods exist for analyzing fluid contamination. At least one method contemplated by the present invention includes using the sensed fluid impedance as a component within an oscillator circuit, thereby impacting the circuit's oscillating frequency which may be used to determine the level of fluid contamination. This method is disclosed in detail in co-pending and co-owned application Ser. No. 08/855,911 entitled "Portable Fluid Screening Device and Method" which is hereby incorporated by reference in its entirety.

Note that impedance is generally measured; therefore the term sensor "impedance" will be used in the remainder this disclosure. It should be noted that although the capacitance of the fluid is analyzed through the impedance, the impedance sensor 10 extends to other fluid impedance variations and therefore, for example, contemplates inductive type sensors within the scope of the present invention.

In FIG. 1, the electrodes 14 and 16 are interdigitated to provide uniformity in impedance measurement. Alternatively, however, the electrodes may take on any suitable configuration and still fall within the scope of the invention. In addition, although the substrate is preferably silicon, the substrate may comprise silicon carbide, germanium, glass or a ceramic material, for example. Further, although aluminum is preferred as electrodes, other conductive materials may be employed as desired, for example, polysilicon, gold, copper, titanium, etc. Further still, although the sensor 10 is illustrated in FIG. 1 as a single sensor, it should be understood that a plurality of such sensors may be integrated onto a single substrate to form an array of sensors.

Figure 2A:
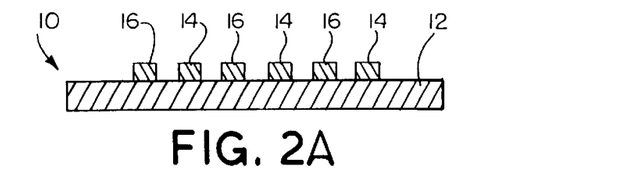
FIG. 2A is a cross section diagram illustrating the micro-miniature sensor of FIG. 1 taken along arrows 2A—2A.

Turning now to FIG. 2A, a cross sectional view of the sensor 10 taken along lines 2A—2A of FIG. 1 is illustrated. The sensor 10 has the electrodes 14 and 16 located along a horizontal plane on the substrate 12. When a lubricant fluid sample contacts the sensor 10, it rests between and above the electrodes 14 and 16, thereby affecting the dielectric constant therebetween. Therefore differing fluid contamination levels will result in different impedance readings of the sensor at its leads (bonds pads 18 and 20) which is then analyzed via analysis circuitry (not shown) to determine within an acceptable accuracy bandwidth the level of fluid contamination which may then be used either as an indication for timely fluid replacement or an indication of machine wear for quality control purposes.

Although the electrodes 14 and 1 6 are illustrated in FIG. 2A as residing entirely within a single horizontal plane, it should be understood that the substrate 12 may undertake a variety of contours and the electrodes 14 and 16 may follow that contour to be customized for various applications as may be desired. Each of these sensor variations are contemplated by the present invention. Alternatively, FIG. 2A illustrates the electrodes 14 and 16 directly on the substrate 12. Although the configuration of FIG. 2A is the preferred embodiment, one may dispose an insulating layer 21 such as silicon nitride between the substrate 12 and the electrodes 14 and 16 as illustrated in sensor 22 of FIG. 2B. The silicon nitride provides for a sensor which can operate at higher operating temperatures.

Figure 2B:
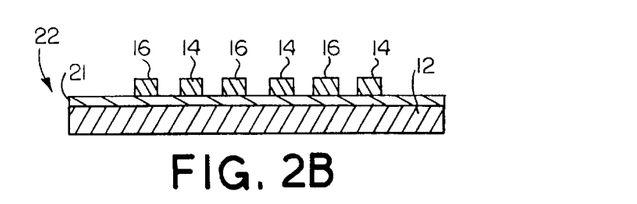
FIG. 2B is a cross section diagram illustrating an alternative micro-miniature sensor according to the invention.
Figure 2C:
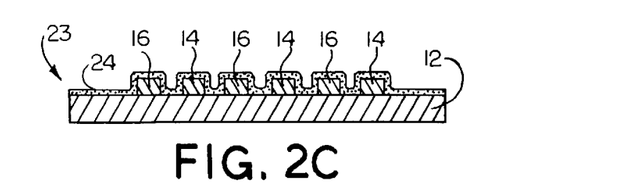
FIG. 2C is a cross section diagram illustrating another alternative micro-miniature sensor according to the invention.

FIG. 2C is a cross-sectional view of an alternative embodiment of a sensor 23 similar to the sensor 10 of FIG. 1. Sensor 23 includes the substrate 12 having the electrodes 14 and 16 formed thereon. Subsequently, an insulating layer 24 (preferably a silicon dioxide layer) is formed over the electrodes 14 and 16 which helps protect the sensor 23 from experiencing "shorts" across the electrodes 14 and 16 caused by substantially sized conductive particulates in a fluid under test. The insulated sensor 23 provides improved performance in detection of non-particulate forms of contamination detection, for example, water content in the fluid or fluid oxidation.

Figures 3A, 3B:
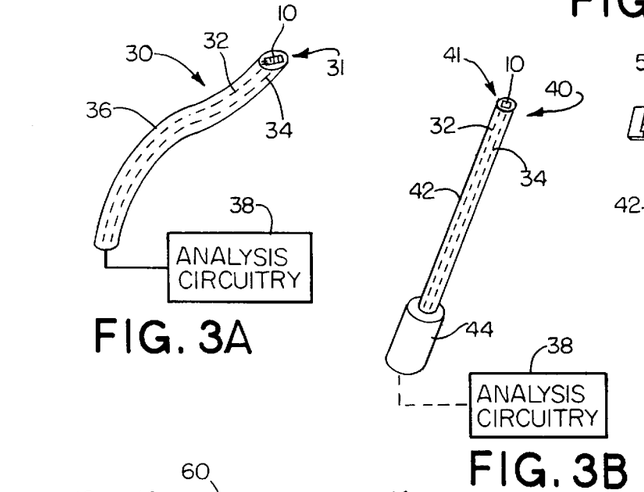
FIG. 3A is a diagram illustrating use of the micro-miniature sensor of FIG. 1 in an elongate probe.
FIG. 3B is a diagram illustrating use of the micro-miniature sensor in a rigid, elongate probe having a handle.

As stated above, the sensors 10, 22 and 23 of FIGS. 2A, 2B and 2C substantially reduce the dimensions of a fluid sensor from approximately 2 in.×2 in. to approximately 1 mm×1 mm, thereby providing substantial improvements in procuring fluid samples for analysis. For example, with the small sensor dimension a probe utilizing such a sensor may easily be inserted into a machine containing a fluid for analysis without either substantially impacting the machine's operation or requiring any disassembly of the machine. FIG. 3A is a diagram which illustrates a probe assembly 30 incorporating the sensor at one end 31. The bond pads 18 and 20 (not shown) of the sensor 10 are coupled to lines 32 and 34 along a flexible probe body 36, thereby transmitting the fluid impedance sensed by the sensor 10 to an analysis circuit 38. The flexible, elongate probe body 36 allows a user to manipulate the probe into numerous shapes to reach difficult-to-reach fluid samples within operating machinery. Further, since the dimensions of the sensor 10 are insubstantial, the sensor 10 does not negatively impact the size of the probe 30 at the end 31, thereby facilitating in obtaining fluid samples in difficult-to-reach locations without adversely impacting a machine's operation or requiring a disassembly of the machine.

In FIG. 3A the analysis circuitry 38 is illustrated as being separate from the probe. Alternatively, since the sensor 10 may reside on a semiconductor substrate, the analysis circuitry may reside at the end 31 of the probe 30 as a circuit integrated with the sensor 10. This alternative embodiment advantageously provides for fluid contamination level determinations to be made local to the measurement site itself, thereby improving analysis accuracy by eliminating errors due to electrical line losses and noise.

FIG. 3B, much like FIG. 3A, is a diagram illustrating an alternative probe assembly 40 having a sensor 10 at one end 41. The sensor 10 is connected to lines 32 and 34 via bond pads 18 and 20 (not shown) which extend through a substantially rigid channel member 42 to a handle 44. The handle 44 provides for ease of use and connects the lines 32 and 34 containing the sensed fluid impedance to the analysis circuitry 38. Alternatively, handle 44 may contain a communications circuit therein to provide wireless transmission of the fluid impedance data to the analysis circuitry 38 through an RF data link, for example. Such wireless capability provides even greater flexibility by allowing a user to be unimpeded by any wire length, etc. which is useful and safe in a factory setting utilizing heavy machinery having moving parts. Although the rigid channel member 42 is not as ductile as the elongate body 36 of FIG. 2A, the channel member 42 provides for firm, precise positional control of the sensor 10 location and the handle 44 allows a user to easily manipulate the probe assembly 40 while avoiding hazards present by moving parts within the machinery.

Figure 3C:
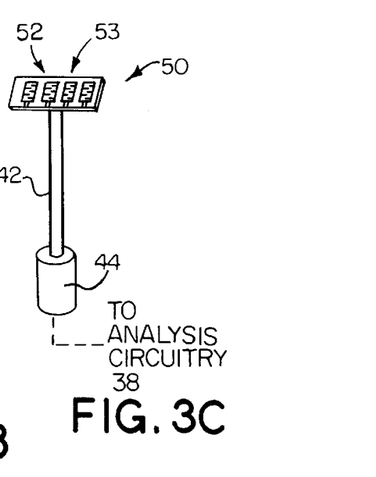
FIG. 3C is a diagram illustrating a micro-miniature sensor array at one end of a probe.

Another advantage provided by the dimensional feature of the sensor 10 is that an array of such sensors may be incorporated together within a single probe assembly without substantially impacting the probe size. FIG. 3C illustrates such a probe assembly 50 wherein an array 52 of sensors 10 reside at one end 53 of the probe assembly 50. Please note that FIG. 3C greatly exaggerates in a dimensional context the array 52 with respect to the other members in order to illustrate the array 52 of sensors 10. In actual practice, the sensor array 52 will reside at the end 53 of the probe assembly 50 and not be substantially larger than the channel member 42. A sensor array 52 may be utilized to provide improved analysis accuracy by providing impedance measurement redundancy. For example, since a fluid contamination concentration is not always uniform (such as when a substantially large particulate is identified which skews the aggregate contamination determination), the sensor array 52 allows for multiple fluid impedance readings to be taken and subsequent data processing techniques used to interpret the data to accurately determine the fluid contamination level. For example, multiple readings may be averaged together or if one reading is substantially different from the others it may be ignored. Alternatively, various statistical operations may be performed on the collected data. When utilizing an array 52 as illustrated in FIG. 3C, each sensor 10 at the probe end 53 may be individually hard-wired to analysis circuitry 38 via the channel member 42 and handle 44. Alternatively, a time multiplexer circuit (or other type multiplexing methodology) may be utilized at the end 53 of the probe assembly 50 to reduce the need for multiple lines 32 and 34 in the channel member 42 to thereby keep the probe assembly 50 small.

The sensor array 52 of FIG. 3C may comprise various configurations. In one embodiment, multiple sensors 10 may be formed on a single substrate 12 such as the array 60 of FIG. 4. In this manner multiplexing circuitry may be integrated onto the substrate 12 to take the multiple measured fluid impedances and multiplex them (via either time multiplexing or other multiplexing technique) for transmission via lines 32 and 34 to the analysis circuitry 38. Further still, the analysis circuitry 38 may also be integrated onto the substrate 12 such that data acquisition and fluid contamination determination may be made at the end 53 of the probe assembly 50, thereby reducing fluid determination errors due to line loss, noise, etc. Alternatively, multiple discrete sensors 10 having separate substrates 12 may reside on another support structure and be affixed to the end 53 of the probe assembly 50.

Figure 4:
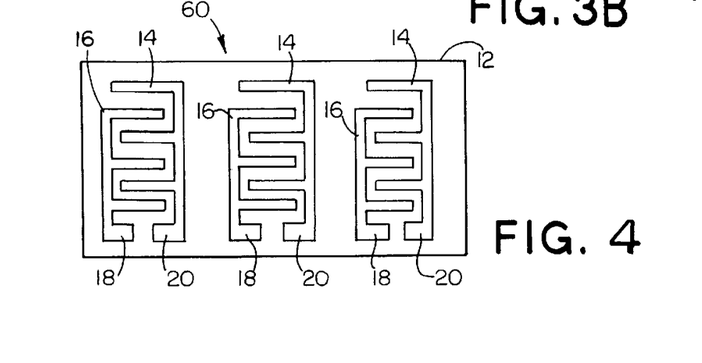
FIG. 4 is a top view illustrating an array of micro-miniature sensors as disclosed in FIG. 1.

The sensor arrays 52 and 60 of FIGS. 3C and 4 may comprise various array configurations as may be desired. For example, as illustrated, the sensor array 52 may be configured in a longitudinal row or be stacked vertically. In addition, the sensor array 52 may extend into two dimensions to form a square shaped sensor or any type of pattern depending upon the desired circumstances. In yet another alternative embodiment the sensor array may extend into three dimensions by stacking the sensors above one another such that sufficient space is provided for fluid contact to the various sensors. Any configuration of sensors 10 to form one dimensional, two dimensional or three dimensional arrays are contemplated by the present invention.

Sensor arrays such as those illustrated in FIGS. 3C and 4 may also be utilized to provide additional information regarding fluid contamination. For example, as illustrated in prior art FIGS. 5 and 6, fluid contamination particulate distributions may be used to identify the sizes and amounts of various particulates to identify machine wearing trends, various machine wear causes and/or modes or whether various machine parts need be replaced. The various prior art particulate distribution analysis methods were inconsistent and required sending a fluid sample off-site for analysis. The sensor array of the present invention, however, overcomes both prior art limitations as illustrated in FIG. 7.

Figure 7:
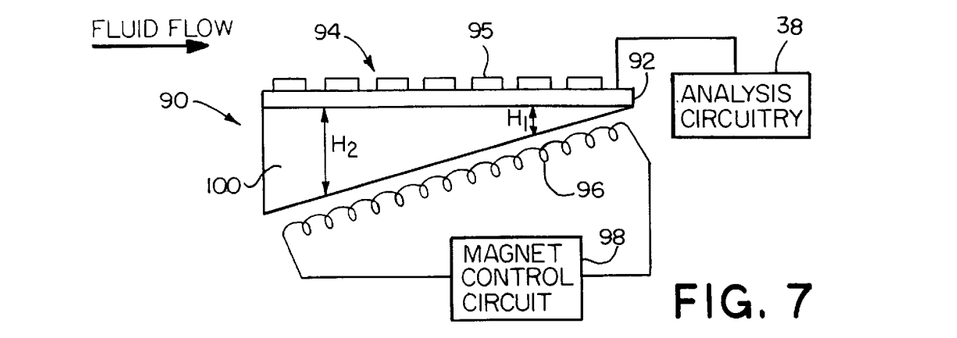
FIG. 7 is a side view of a system according to one aspect of the invention having an array of micro-miniature sensors placed within a magnetic field intensity gradient.

FIG. 7 is a system level diagram which illustrates a fluid contamination analyzer system 90 having a substrate 92 upon which a sensor array 94 resides, wherein each sensor 95 is constructed and behaves as the sensors 10, 22 and 23 of FIGS. 2A, 2B and 2C, respectively. Each sensor 95 is coupled (not shown) to the analysis circuitry 38 either directly or via a multiplexer circuit that may reside on the substrate 92. A magnetic field source 96, preferably an electromagnet coil, is coupled to a magnetic control circuit 98 to selectively activate a magnetic field source 96 such that the magnetic field may be turned on and off as desired. The magnetic field source 96 is preferably oriented to provide a magnetic field intensity gradient along a length of the sensor array 94. Preferably, the orientation is determined by a spacer wedge 100 as illustrated, however, other mechanisms such as brackets, etc. may also be utilized and are contemplated by the present invention.

The sensor array 94 of FIG. 7 operates in the following manner. A lubricant fluid for analysis is brought into contact with the sensor array 94. This may be accomplished by either placing the fluid contamination analyzer system 90 on a probe and inserting the sensor array 94 into the fluid or preferably affixing the system 90 to a machine in the fluid flow path to thereby provide an on-line fluid analyzer. In yet another alternative, the fluid may be removed from the machine and brought into contact with the sensor array 94. The magnetic control circuit 98 activates the coil 96, thereby generating a magnetic field. The sensor array 94, due to its positional orientation with respect to the coil 96, experiences a magnetic field intensity gradient along its length such that at one end a large magnetic field intensity ($H_1$) is experienced at the substrate 92 while at another end a substantially smaller magnetic field intensity ($H_2$) is experienced at the substrate 92. Due to the magnetic field intensity gradient, ferromagnetic particulates (contaminants) of differing sizes in the fluid are distilled from the fluid flow path onto the sensor array 94 such that a particulate distribution is generated across the sensor array 94. Therefore each sensor 95 in the sensor array 94 will have a unique impedance due to the size and quantity of the particulates at that location. This impedance information is then used by the analysis circuitry 38 and processors to determine how much contamination exists at differing particulate sizes which may be utilized to determine wear modes, wear trends, etc. After the impedance data has been collected, the magnetic control circuit 98 deactivates the coil 96 thereby turning the magnetic field off. Without any magnetic field acting on the particulates, the force of fluid flow substantially removes particulates from the sensor array 94.

Various modifications and alternative embodiments may be employed with the sensor array 94. In one alternative, a magnetic field intensity gradient may be achieved by utilizing a plurality of independent magnetic field sources fixed at varying distances from the substrate 92 or wherein each source has a unique magnetic field intensity such that their aggregation provides a magnetic field intensity gradient. Any type of magnetic field source or configuration of sources that would provide a variable magnetic field intensity across the sensor array 94 is contemplated in the present invention. Furthermore, although a coil is the preferred magnetic field source 96, any other type of magnetic source falls within the scope of the present invention.

Preferably, the system 90 of FIG. 7 advantageously allows for the magnetic source 96 to be turned off to thereby allow for particulates attracted to the sensor array 94 by the magnetic field to be released (e.g., washed away by fluid flow).

In yet another alternative embodiment, one or more of the sensors in the sensor array 94 may be covered with an insulating film or layer as illustrated in FIG. 2C to provide non-particulate contamination information such as the water content of the fluid and/or fluid oxidation for analysis.

Figure 8:
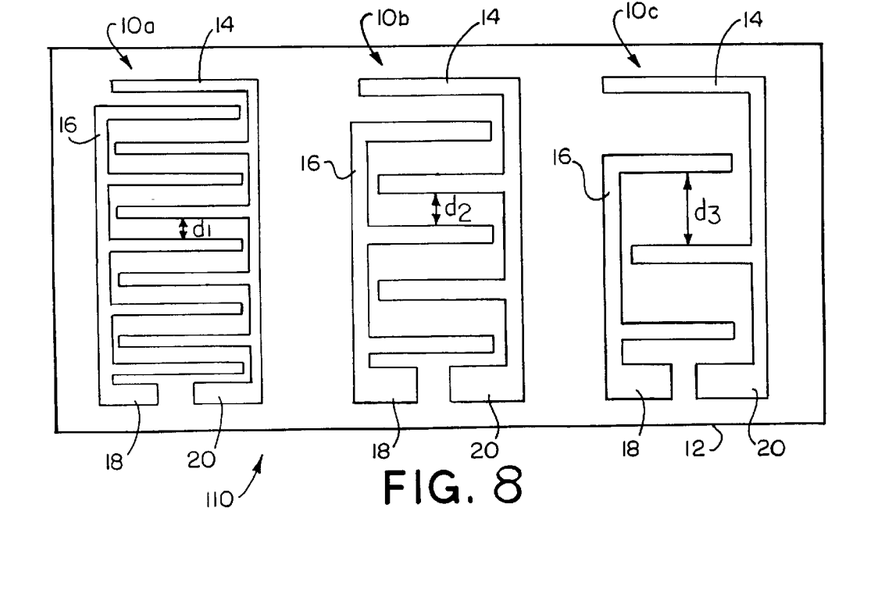
FIG. 8 is a top view of an alternative embodiment of the invention, wherein an array of micro-miniature sensors have variations in electrode spacings.

In addition to the sensor array 94 of FIG. 7, another alternative embodiment may be employed in conjunction with the fluid analyzer system 90 of FIG. 7 and is illustrated in FIG. 8. FIG. 8 is a top view of a sensor array 110 wherein a substrate 12 contains a plurality of sensors 10 formed thereon. Each sensor 10 is much like the sensor of FIG. 1 (or alternatively sensors 22 or 23 of FIGS. 2B and 2C), having a substrate 12, conductors (electrodes) 14 and 16 and bond pads 18 and 20. The sensor array 110 differs from the sensor array 60 of FIG. 4 in that at least one of the sensors varies from the others with respect to the spacing between the interdigitated electrodes. For example, as illustrated in FIG. 8, sensor 10a has a somewhat close conductor spacing ($d_1$) for fine sized particulates, sensor 10b has a larger electrode spacing ($d_2$) for medium sized particulates and sensor 10c has an even larger electrode spacing ($d_3$) to accommodate large size particulates (wherein $d_1<d_2<d_3$). Such a variable electrode spacing sensor array 110 further accommodates particulate contamination distribution determinations by helping to delineate the size of the particulates due to the difference in spacing of the electrodes 14 and 16. Therefore to carry out this feature, the sensor 10c is preferably located within the array 110 near the largest magnetic field intensity which has sufficient strength to distill large sized contaminants from the fluid while sensor 10a preferably is located within the array 110 near the weakest magnetic field intensity which has sufficient strength to distill small size contaminants from the fluid.

Figure 9:
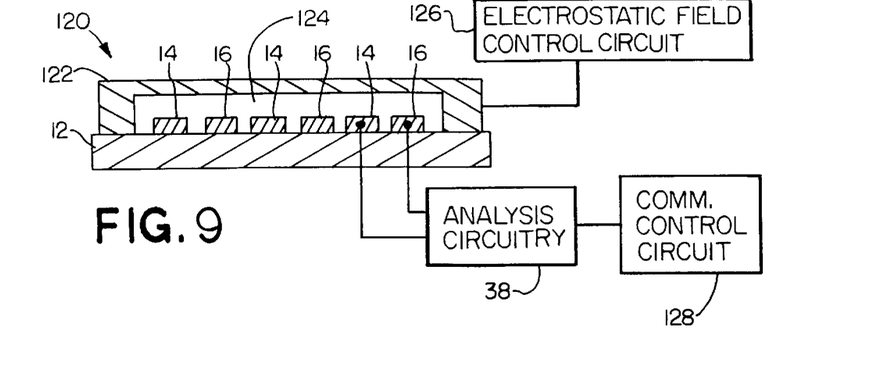
FIG. 9 is a combined cross section and schematic view of a micro-miniature sensor array having an overlying conductive layer for dislodging of charged particulates via an electrostatic force and circuitry for controlling the electrostatic force, analyzing the sensor impedances and communicating the results.

Turning now to FIG. 9, an alternative sensor is disclosed. In on-line fluid contamination analyzers such as the system 90 of FIG. 7, fluid particulates are typically swept away by the fluid flow after the magnetic field source 96 is deactivated. In some cases, however, static charge develops on the conductive or ferromagnetic particles such that although the magnetic field may no longer exist to impart a force on the particles, the static charge on the particles is sufficient to lodge the particles in the surface of the sensor which causes errors in subsequent contamination measurements as charged particles build up on the sensor. The sensor 120 of FIG. 9 may operate in the context of the system 90 of FIG. 7 and includes a substrate 12 having a plurality of conductors 14 and 16 disposed thereon. A conductive layer 122 is then formed over conductor electrodes 14 and 16 such that a cavity 124 is formed between the conductive layer 124 and the electrodes. The conductive layer 122 may be formed via one of various semiconductor processing techniques. One method may include depositing an insulating material over the electrodes 14 and 16, depositing a conductive layer over the insulating layer, etching the conductive layer to form the conductive layer 122 and wet etching the underlying insulating layer away to thereby form the cavity 124 between the electrodes 14 and 16 and the conductive layer 122 through which the fluid under test will flow. The conductive layer 122 is coupled to an electrostatic field control circuit 126 while the electrodes 14 and 16 are coupled to analysis circuitry 38 which in turn is connected, in this embodiment, to a communications control circuit 128.

The sensor 120 operates in the following manner. After a magnetic field source (not shown) is deactivated, particulates are preferably washed away due to fluid flow through the cavity 124. There are frequently, however, particulates that contain a residual static charge large enough to remain stuck to one of the electrodes 14 and 16 despite the fluid flow through the cavity 124. The electrostatic field control circuit 126 then applies a voltage to the conductive layer 122 such that an electrostatic field is generated in the cavity 124 that is sufficiently large such that particulates are dislodged and washed away by the fluid flow through the cavity 124. In this manner, fluid contamination accuracy is improved by eliminating the chance of residual particulates from previous fluid sample measurements interfering with subsequent fluid measurements by washing performed periodically via the electrostatic control circuit 126 and the conductive layer 122.

Figure 10:
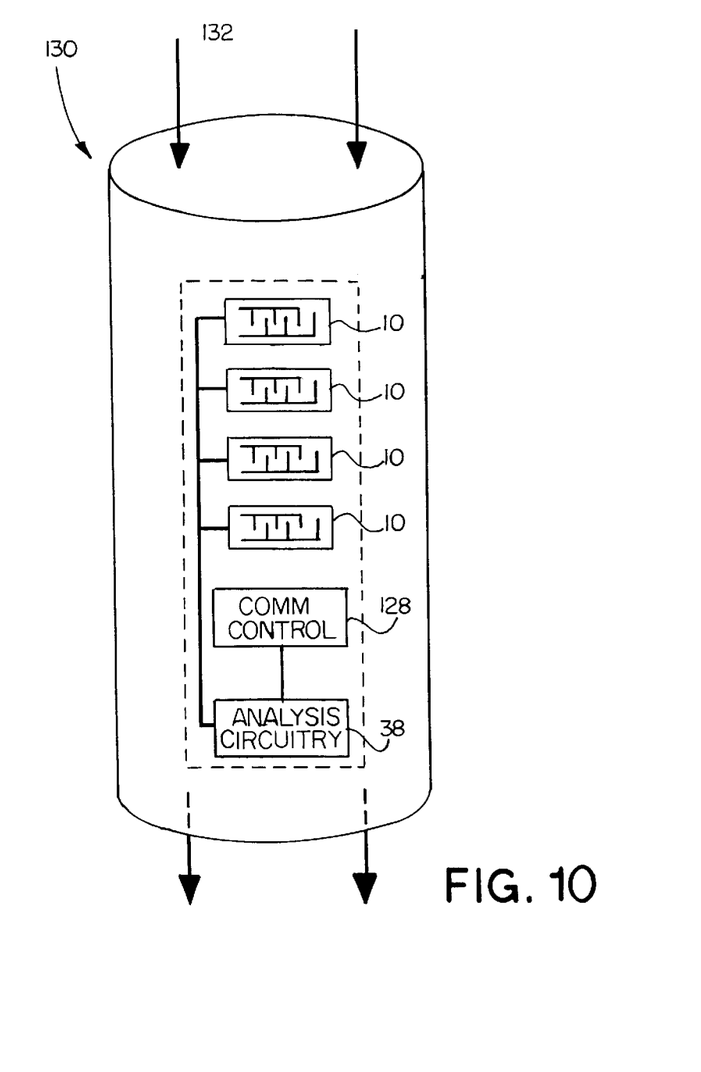
FIG. 10 is a perspective view of an on-line fluid analyzer having an array of micro-miniature sensors in a lubricant fluid flow path having both circuitry for analyzing the impedance and communicating the results to other circuitry.

FIG. 10 is a perspective view of the sensor system 130 in an on-line configuration in which the sensors 10 themselves are in a fluid flow path 132 of a machine. As discussed supra, the sensor 10 senses the fluid impedance which is read by the analysis circuit 38 which analyzes and/or processes the data to arrive at a fluid contamination determination. This result may then be communicated either visually to a user who is taking a fluid contamination reading via a display (not shown) or may alternatively communicate the result to a central data collection station (not shown) via the communications control circuit 128 which is operable to transmit data, preferably via an RF signal, to the data collection station.

Figure 11:
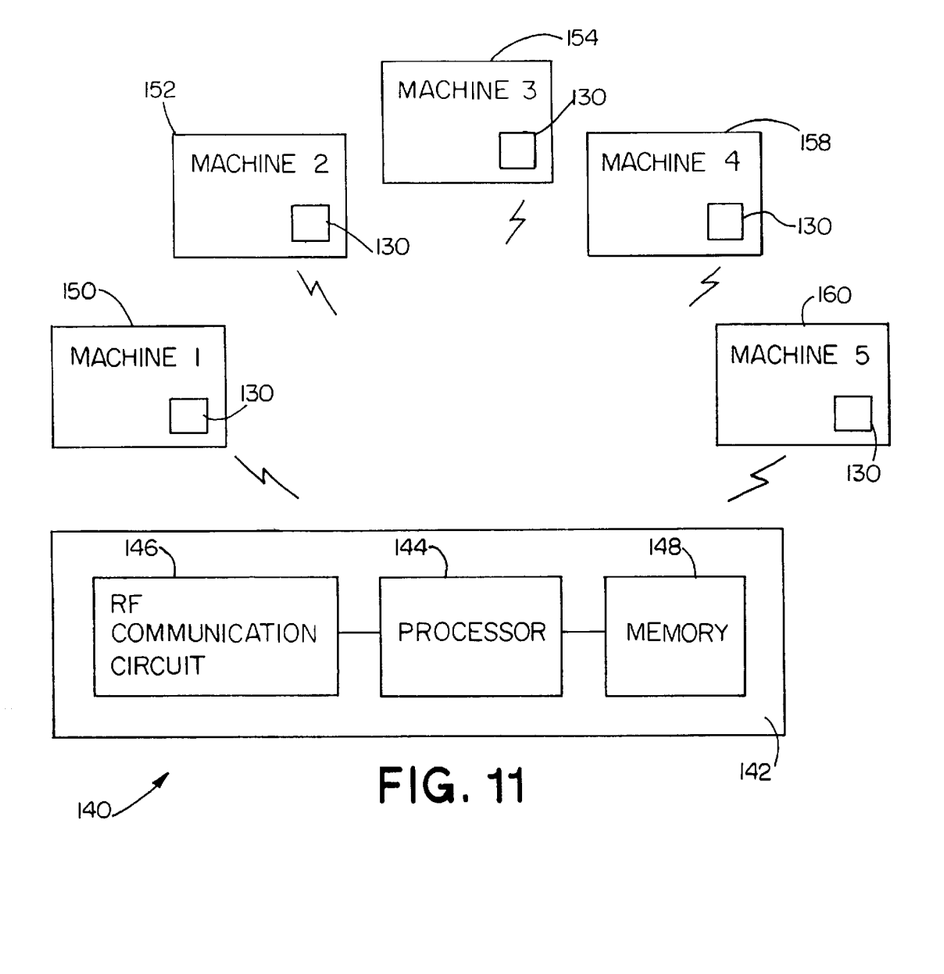
FIG. 11 is a block, system level diagram illustrating an environmental view of the invention, wherein a plurality of machines contain micro-miniature sensors for sensing fluid contamination and circuitry for communicating the results to a central data analysis and storage site.

FIG. 11 is a system level diagram which illustrates a dynamic fluid contamination analysis system 140. System 140 includes a central data collection, processing and storage unit 142 which contains a processor 144, an RF communications circuit 146 and a memory 148. The central data collection unit 142 may also include an I/O port, an input peripheral device and a display for interacting with a user. The system 140 includes a plurality of machines 150, 152, 154, 158 and 160 which operate in a factory setting and utilize fluids of lubricant and cooling purposes. Each machine contains a sensor system 130 (as illustrated in FIG. 10, for example) that performs in an on-line configuration. Periodically, as dictated by the processor 144 and RF communications circuit 146, the sensor systems 130 are instructed to measure the fluid impedance of the fluid in their respective machines. Each sensor system 130 then communicates its present fluid impedance to the processor 144 via its communications control circuit 128. The processor 144 then makes a fluid contamination determination, stores it in the memory 148 for trending purposes and indicates the determination to monitoring personnel if the fluid contamination level exceeds a predetermined threshold. In this manner, the fluid contamination analysis system 140 monitors a plurality of machines without requiring a user to go from machine to machine taking fluid samples and interfering with the machine operation. In addition, since the sensor arrays of the present invention are small, they may serve in on-line configurations without interfering with machine operation.

The various features of the present invention may be utilized in a variety of applications, configurations and packages. Each variation is contemplated as falling within the scope of the present invention. For example, the sensors may be potted or secured in a DIP (dual in-line package) for easy insertion and replacement.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A fluid contamination analyzer, comprising:
    a probe; and
    at least one micro-miniature sensor at one end of the probe, wherein the at least one sensor includes:
        a substrate;
        a plurality of conductors formed over the substrate, wherein each is coupled to one of two leads; and
        an insulating layer disposed between the plurality of conductors and the substrate;
    wherein the conductors form electrodes of the sensor and when a fluid contacts the sensor an impedance of the fluid may be determined using the leads of the sensor, thereby providing an indication of fluid contamination.

2. An on-line fluid contamination analyzer, comprising:
    an array of micro-miniature sensors located within a path of fluid flow; and
    a selectively activatable electromagnet in proximity to the array of micro-miniature sensors, wherein the electromagnet may be activated and deactivated in response to control signals and provides a magnetic gradient across the sensor array, and wherein the magnetic gradient provides a contaminant size distribution across the sensor array.

3. A fluid contamination analyzer, comprising:
    a probe;
    at least one micro-miniature sensor at one end of the probe, wherein the at least one sensor includes:
        a substrate;
        a plurality of conductors formed over the substrate, wherein each is coupled to one of two leads; and
        an insulating layer overlying the plurality of conductors; and
    a conductive layer overlying the conductors, thereby forming a cavity for fluid flow analysis between the conductive layer and the conductors,
    wherein the conductors form electrodes of the sensor and when a fluid contacts the sensor an impedance of the fluid may be determined using the leads of the sensor, thereby providing an indication of fluid contamination; and
    when a voltage is applied to the conductive layer, an electrostatic field develops within the cavity, thereby dislodging any particulates that may have become stuck in the sensor and thereby improving fluid contamination analysis accuracy.

4. A fluid contamination analyzer including a micro-miniature sensor, comprising:
    a substrate;
    a plurality of conductors formed over the substrate, wherein each is coupled to one of two leads, wherein the conductors form electrodes of the sensor and when a fluid contacts the sensor an impedance of the fluid may be determined using the leads of the sensor, thereby providing an indication of fluid contamination; and
    a conductive layer overlying the conductors, thereby creating a cavity for fluid flow analysis between the conductive layer and the conductors, wherein when a voltage is applied to the conductive layer, an electrostatic field develops within the cavity, thereby dislodging with an electrostatic force any particulates that may have become stuck within the sensor due to static charge on the particulates and thereby improving fluid contamination analysis accuracy.

5. An on-line contamination analyzer, comprising:
    an array of micro-miniature sensors located within a path of fluid flow, wherein each sensor includes a plurality of conductors which serve as electrodes and wherein a spacing between the electrodes within each sensor is constant and at least one of the sensors has an electrode spacing which varies from another sensor electrode spacing; and a selectively activatable electromagnet in proximity to the array of micro-miniature sensors, wherein the electromagnet may be activated and deactivated in response to control signals and provides a magnetic field intensity gradient across the sensor array, thereby resulting in a contaminant size distribution across the sensor array.

6. The analyzer of claim 5, further comprising an insulative layer disposed between the plurality of conductors and the substrate.

7. The analyzer of claim 5, further comprising an insulative layer overlying the plurality of conductors.

8. The analyzer of claim 5, further comprising a conductive layer overlying the conductors, thereby forming a cavity for fluid flow analysis between the conductive layer and the conductors, wherein when a voltage is applied to the conductive layer, an electrostatic filed develops within the cavity, thereby dislodging any particulates that may have become stuck in the sensor and thereby improving fluid contamination analysis accuracy.

9. The analyzer of claim 4, further comprising an array of micro-miniature sensors located within a path of fluid flow, wherein the array of sensors are utilized to improve the accuracy of fluid contamination analysis by providing multiple data samples for subsequent statistical analysis.

10. The analyzer of claim 1, further comprising an array of micro-miniature sensors located within a path of fluid flow, wherein the array of sensors are utilized to improve the accuracy of fluid contamination analysis by providing multiple data samples for subsequent statistical analysis.

11. The analyzer of claim 10, wherein at least one of the sensors has a spacing between the conductors that differs from the other sensors.

12. A fluid contamination analyzer, comprising:
a probe;
at least one micro-miniature sensor at one end of the probe, wherein the at least one sensor includes:
a substrate;
a plurality of conductors formed over the substrate, wherein each is coupled to one of two leads; and
an insulating layer overlying the plurality of conductors;
an array of micro-miniature sensors located within a path of fluid flow, wherein the array of sensors are utilized to improve the accuracy of fluid contamination analysis by providing multiple data samples for subsequent statistical analysis; and an electromagnet in proximity to the array of sensors, wherein the electromagnet provides a magnetic gradient across the sensor array, thereby providing a fluid contaminant size distribution across the sensor array,
wherein the conductors form electrodes of the sensor and when a fluid contacts the sensor an impedance of the fluid may be determined using the leads of the sensor, thereby providing an indication of fluid contamination.

13. The analyzer of claim 12, wherein the electromagnet is selectively activatable, thereby allowing the electromagnet to be turned on and off.

14. The analyzer of claim 2, wherein at least one of the array of micro-miniature sensors comprise:
a substrate; and
a plurality of conductors formed over the substrate, wherein each is coupled to one of two leads,
wherein the conductors form electrodes of the sensor and when a fluid contacts the sensor an impedance of the fluid may be determined using the leads of the sensor, thereby providing an indication of fluid contamination.

15. The analyzer of claim 14, further comprising an insulative layer disposed between the plurality of conductors and the substrate.

16. The analyzer of claim 14, further comprising an insulative layer overlying the plurality of conductors.

17. The analyzer of claim 14, further comprising a conductive layer overlying the conductors, thereby forming a cavity for fluid flow analysis between the conductive layer and the conductors, wherein when a voltage is applied to the conductive layer, an electrostatic filed develops within the cavity, thereby dislodging any particulates that may have become stuck in the sensor and thereby improving fluid contamination analysis accuracy.

18. The analyzer of claim 14, wherein at least one of the sensors has a spacing between the conductors that differs from the other sensors.

19. The analyzer of claim 4, further comprising an insulative layer disposed between the plurality of conductors and the substrate.

20. The analyzer of claim 4, further comprising an insulative layer overlying the plurality of conductors.

21. The analyzer of claim 9, wherein at least one of the sensors has a spacing between the conductors that differs from the other sensors.

* * * * *